United States Patent [19]

Paradis

[11] Patent Number: 5,070,905
[45] Date of Patent: Dec. 10, 1991

[54] DIRECTIONAL FLOW CONTROL
[76] Inventor: Joseph Paradis, Hilton Head, S.C.
[21] Appl. No.: 530,097
[22] Filed: May 29, 1990
[51] Int. Cl.⁵ ............................................. F16K 15/14
[52] U.S. Cl. ................................... 137/606; 137/843; 604/86; 604/247
[58] Field of Search ................. 137/12, 843, 606; 604/83, 86, 247

[56] References Cited

U.S. PATENT DOCUMENTS

| | | | |
|---|---|---|---|
| 3,886,937 | 6/1975 | Bobo | 137/843 X |
| 4,000,740 | 1/1977 | Mittleman | 604/86 |
| 4,405,316 | 9/1983 | Mittleman | 604/86 |
| 4,415,003 | 11/1983 | Paradis | 137/843 |
| 4,596,265 | 6/1986 | Goodell | 137/843 X |
| 4,610,276 | 9/1986 | Paradis | 604/86 X |
| 4,958,661 | 9/1990 | Holtermann | 137/843 |

FOREIGN PATENT DOCUMENTS 0109903 11/1983 European Pat. Off. ............. 604/86

Primary Examiner—Robert G. Nilson
Attorney, Agent, or Firm—George E. Kersey

[57] ABSTRACT

A flow control device in which a plurality of flow channels converge in a two-part housing containing a free-floating and pre-biased flow control diaphragm and an injection site. The free-floating diaphragm is at the entry position of an intermediate channel which extends to an output channel of the injection site. The control diaphragm is pre-biased by a prong which extends from a base portion of the two-part housing.

14 Claims, 4 Drawing Sheets

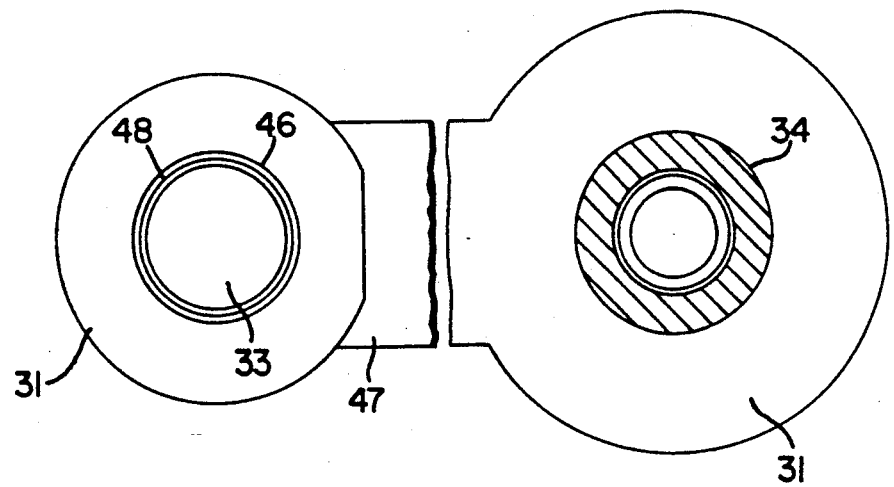
FIG. 5A
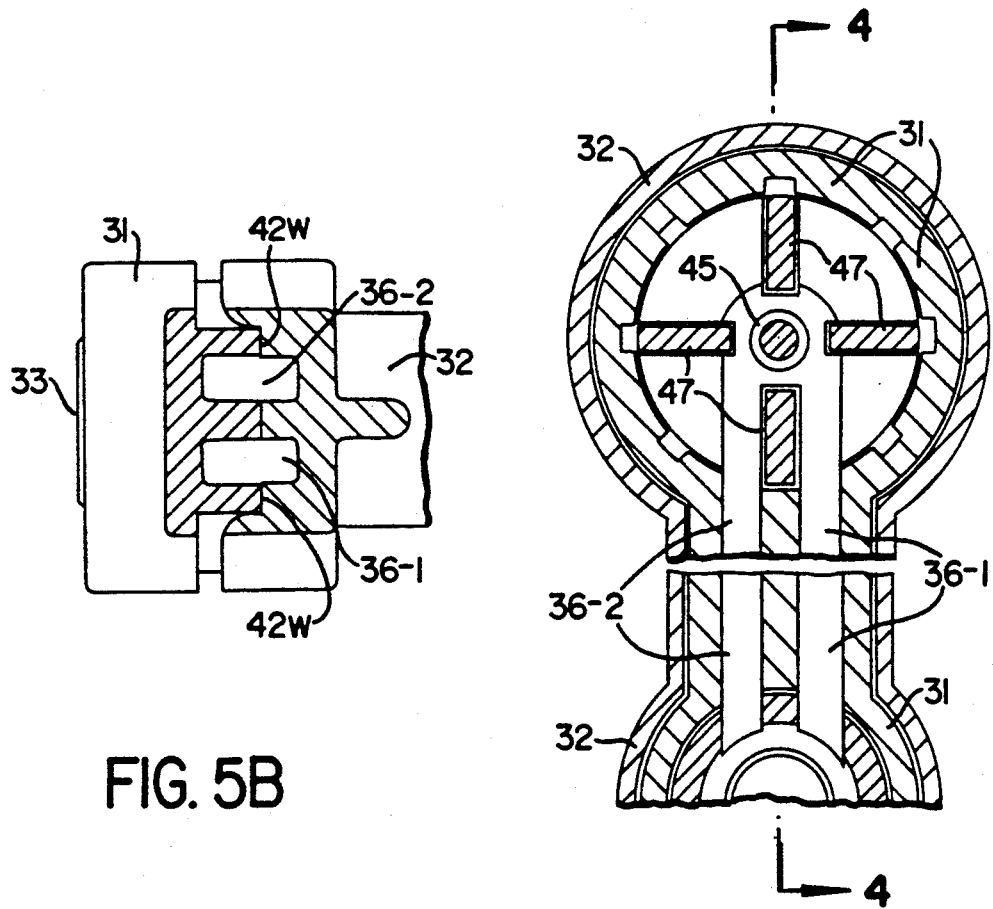
FIG. 5B
FIG. 5C

DIRECTIONAL FLOW CONTROL

BACKGROUND OF THE INVENTION

This invention relates to flow control and more particularly, to the directional control of fluid flow and injected fluids.

It often is desirable to control the flow of fluid such as liquids and gases. A common device for that purpose is known as a check valve. It functions by the deflection of an elastomeric element towards and away from a valve seat. The deflection is towards the valve seat in order to prevent flow, and away from the seat to permit flow.

In some cases the control of fluid flow is with respect to a multiplicity of channels that have varying degrees of convergence with one another. A typical multichannel arrangement makes use of connectors which permit the intercoupling of flow channels as desired. For example, when two channels are to be joined selectively to permit a common output from a single channel, the connector can take the form of a fitting that resembles a "Y".

The inclusion of control valves in the various lines leading to a coupler can pose a number of complications. The inclusion of separate control elements can cause difficulties in assuring proper sealing. A common point of leakage in a line often occurs where the line has been severed in order to receive a control element. In addition, the inclusion of separate control elements in various lines leading to a coupler does not always provide the most efficient control over fluid flow.

One solution for overcoming difficulties associated with prior art valves that control flow on multiple channels is set forth in U.S. Pat. No. 4,610,276 which issued Sept. 9, 1986. This patent discloses a directional flow control valve with a main channel for the through-flow of fluid and a branch channel connected to the main channel at an intermediate position. This permits the convergence of flow through the main channel with flow through the branch channel. At the convergence of the two channels, there is a diaphragm for controlling the flow between the two channels. The diaphragm is clamped and bowed under pressure into the inlet of the branch channel. The application of pressure to the diaphragm assures the sealing of the branch channel against flow diverted from the main channel.

There also is a common housing in the '276 patent for the main flow channel and the branch flow channel. The diaphragm is bowed into the branch channel by a set of prongs with tips that extend as projections from a shelf that is common to the branch and main channels. The bowing of the diaphragm is asymmetric, and greater pressure is applied away from the region of outflow from the branch channel.

While the diaphragm of the 4,610,276 patent operates properly in most cases, there is the possibility that the diaphragm will fail to seat properly.

Another valve arrangement for dealing with main and branch channels is disclosed in U.S. Pat. No. 4,874,369 which issued Oct. 17, 1989. This arrangement employs an injection site in conjunction with a valve, illustratively of the duck-bill type, in a configuration that is complex, costly and difficult to manufacture. In addition, duck-bill valves of the type contemplated by the '369 patent have proved to be unreliable in practice, with such difficulties as failure to seal properly.

Other arrangements which relate to the control of fluid flow are disclosed in Osborne U.S. Pat. No. 2,270,468; Goott et al U.S. Pat. No. 3,370,305; Craft U.S. Pat. No. 3,457,933; Rosenberg 3,572,375, 3,650,093 and 3,710,942; Melnick U.S. Pat. No. 3,891,000; Mittleman U.S. Pat. No. 4,000,740 and 4,405,316; Stevens 4,000,739; Zedes et al U.S. Pat. No. 4,005,710; Mittleman et al 4,048,996 and 4,133,441; Rushkie et al U.S. Pat. No. 4,222,407; Sheehan et al 4,294,249; Spademan 4,338,934; Spector et al 4,424,833; Edwards et al 4,566,493 and Suzuki et al 4,610,674; EPO 0109903; France 2004771 and UK 2033230. None of these arragements provide enhanced flow control where there is diversion of fluid flow from one direction to another.

Accordingly, it is an object of the invention to enhance the control that can be achieved over fluid. A related object is to enhance flow control where there is a diversion of fluid flow from one direction to another.

A further object is to achieve greater reliability over valve operation than is achievable by clamped diaphragm and duck-bill valves.

Still another object is to achieve precision control at reduced cost and simplification.

A further object of the invention is to improve the performance of injection site valves.

SUMMARY OF THE INVENTION

In accomplishing the foregoing and related objects the invention provides a flow control device which includes a first channel for the flow of fluid, a branch channel angularly disposed with respect to the first channel to serve as a conduit for at least a portion of the flow from the first channel, and a freely floatable diaphragm, which is bowed under pressure into the first channel at the convergence of the branch and first channels for controlling the flow from the first channel into the branch channel.

In accordance with one aspect of the invention the diaphragm is bowed under pressure by a prong extending in the axial direction of the first channel, and the diaphragm is positioned by the prong against an annular seat. The seat desirably has a circumferential skirt that limits the lateral movement of the diaphragm, which is spaced from buttresses that limit the movement of the diaphragm in the axial direction of the first channel. The butresses advantageously are equally positioned and circumferentially arranged with respect to the diaphragm.

In accordance with a further aspect of the invention the branch channel has opposite ends, of which one end is connected to the first channel, and there is a second channel connected to the other end of the branch channel. The branch channel desirably is formed by two subordinate parallel channels.

In accordance with yet another aspect of the invention the first channel is terminated in a base and the second channel is terminated in a cap.

The device is formed as a two-part member with the first part including a stem of the first channel, an outer portion of the branch channel and the cap of the second channel. The second part of the device includes a stem of the second channel, the remaining portion of the branch channel and the base of the first channel.

In a method of controlling fluid flow in accordance with the invention, fluid is introduced into a first channel; diverted into a second channel; and the flow of fluid from the first channel into the second channel is controlled by a freely floatable diaphragm which is bowed under pressure into the first channel.

DESCRIPTION OF THE DRAWINGS

FIG. 5A is a cross-sectional view of the flow control device of FIG. 4 taken along the lines 5A—5A;

FIG. 5B is a cross-sectional view of the flow control device of FIG. 4 taken along the lines 5B—5B;

FIG. 5C is a cross-sectional view of the flow control device of FIG. 4 taken along the lines 5C—5C.

DETAILED DESCRIPTION (a) The Prior Art

Figure 1:
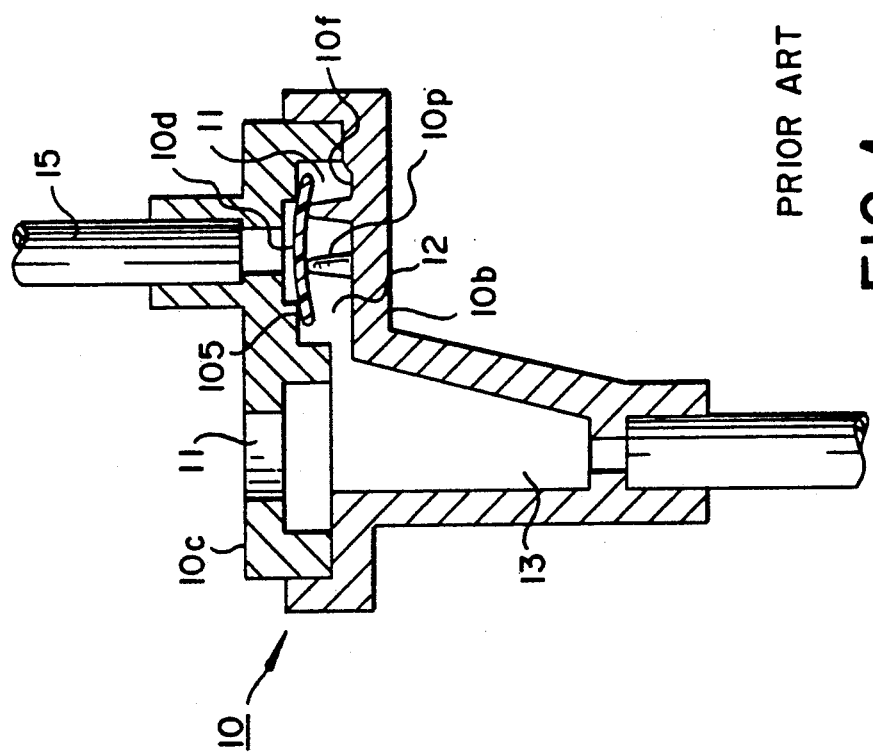
FIG. 1 is a cross-sectional view of a directional flow-control valve and coupling device in accordance with the prior art.

With reference to the drawings, a coupling device 10 in accordance with the prior art is shown in FIG. 1. The device 10 is formed by a base 10b and a cap 10c. The cap 10c contains appertures for a first flow channel 11 and an injection site for a branch flow channel 12. Flow from the respective channels 11 and 12 is selectively combined in an output channel 13 in accordance with the operation of a control diaphragm 10d.

The diaphragm 10d seals the channel 12 according to whether there is upward flow in the channel 13, or downward flow in the tubing 15. In the case of downward flow, the diaphragm 10d is moved away from its seat 10s in the cap 10c as pictured in FIG. 1. Conversely, when the downward flow in the tubing 15 is terminated, or when there is upward flow in the output channel 13, the diaphragm 10d again becomes seated and there is no outflow along the tubing 15. This kind of diaphragm operation is commonly provided by a check valve but in FIG. 1 is provided by the multifunctional coupling structure 10.

In order to properly seat the diaphragm 10d when there is no downward flow along the tubing 15, the base member 10g includes prebiasing prongs 10p on a platform 10f of the base 10b. "Prebiasing" means that there is a small force, i.e., bias, exerted against the diaphragm 10d by the prongs 10p when the diaphragm is in its equilibrium position. When flow takes place to the channel 12, it is directed into the output channel 13 from the tubing 15 by ribs 10r which extend upwardly from the base 10b into contact with the cap 10c when it is positioned on the device 10 as shown in FIG. 1. The channel 11 can be an injection site for the introduction of a substance to be mixed with fluid flowing in the tubing 15.

The combination injection site and the check valve in FIG. 1 achieves a number of advantages. The close proximity of the site and valve prevents any retrograde flow to the tubing and improves purging. This is important in the case of drugs that require minimum diluent, or that must be administered quickly to a patient. In the case of viscous and highly dense drugs that flow from intravenous tubing, a considerable amount of time and fluid are required in order to purge the drug out of tubing. It is important to minimize any stagnant area where drugs or air can collect. This avoids air entrapment.

(b) Alternative Prior Art

Figure 2:
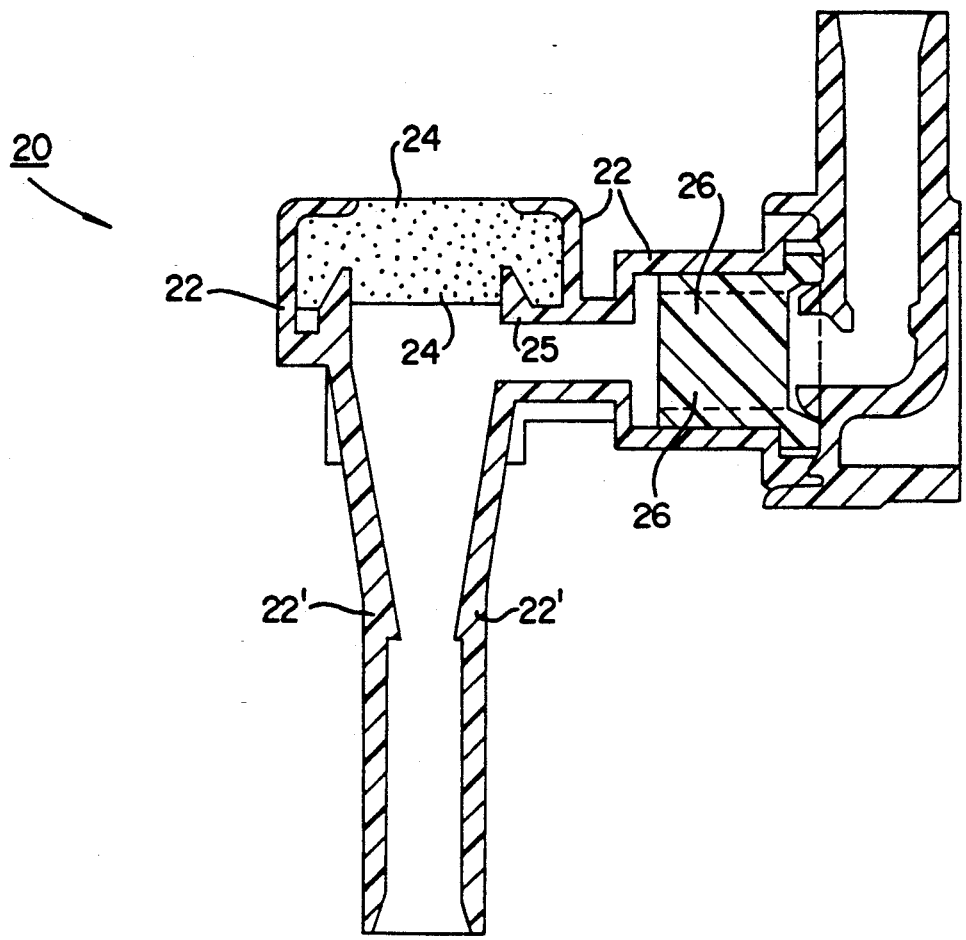
FIG. 2 is a cross-sectional view of an alternative directional flow control valve and coupling device in accordance with the prior art.

An alternative flow control device 20 in accordance with the prior art is shown in FIG. 2. In the device 20, there is a unitary housing 22 that includes a stopper 24 and a valve 26. The stopper 24 serves as an injection site and is connected between two sets of tubing to administer, for example, a parenteral solution to a patient. Generally, the device 20, like the device 10 of FIG. 1, is used for continuous intravenous fluid administration to a patient. When therapy of a patient requires supplemental intravenous medication, or other intermittent fluid administration, a syringe or other injection apparatus is used to insert medication into the intravenous fluid. This is accomplished by inserting and then withdrawing a needle through the stopper 24. Since the intravenous solution may be administered for lengthy periods, the stopper 24 desirably should withstand numerous needle piercings and removals, even under high pressure.

The housing 22 accommodates both the stopper 24 and the valve 26. The stopper portion of the housing includes a top 21, a cylindrical retainer 28, an intermediate ledge 25 and a cone-shaped outlet 22. The cone-shape of the outlet 22' helps deflect needles into the center of the injection site. This prevents needles from piercing the side walls of the site.

The ledge 25 extends circumferentially and has an upwardly turned lip. The stopper 24 is approximately disc-shaped with a grooved bottom surface of the housing 22 that receives a lip of the ledge 25. The top of the housing 22 and the ledge 25 hold the stopper 24 in compression.

The valve 26 includes sides that are positioned at an angle to form a slit through which fluid passes. The sides extend to an annular collar. The end of the valve 26 is near the outlet cone 22.

The enlarged section of the arm 23 requires a flange that surrounds and mates with an annular collar, while tabs of the valve 26 are needed in notches of the arm 23. This arrangement is required to insure that the valve 26 does not twist within the housing 21. The clearance between valve sides and the arm 22 is small. Twisting of the valve 26 is objectionable because it disturbs the proper operation of the valve 26.

The housing for the stopper 24 has an arm 23 joined to a cone-shaped outlet portion 22 immediately below the ledge 25. The arm 23 provides for the main flow of fluid through the injection site and includes an enlarged section that houses the valve 26, illustratively of the duck-bill type as shown and described in U.S. Pat. No. 4,566,493. This kind of valve is expensive to manufacture. It also is complex and difficult to insert into a one-piece device.

In addition the poositioning of the stopper 24 in the housing 21 poses considerable difficulties. Immediately after being molded, the top of the housing is a vertical extension of sides of a cylindrical portion 28. After the stopper 24 is positioned on the ledge 20, the top edge of the cylinder sides is bent inwardly to form the top by ultrasonic deformation, heating or cold forming. The unitary molded of the housing 21 with the stopper 24 in compression is very difficult, costly and does not provide stable assembly dimensions. In addition, the unitary molding of the stopper suffers compression cracks in practice, rendering the resulting device completely unacceptable for use.

(c) Illustrative Embodiment of Invention

Figure 3:
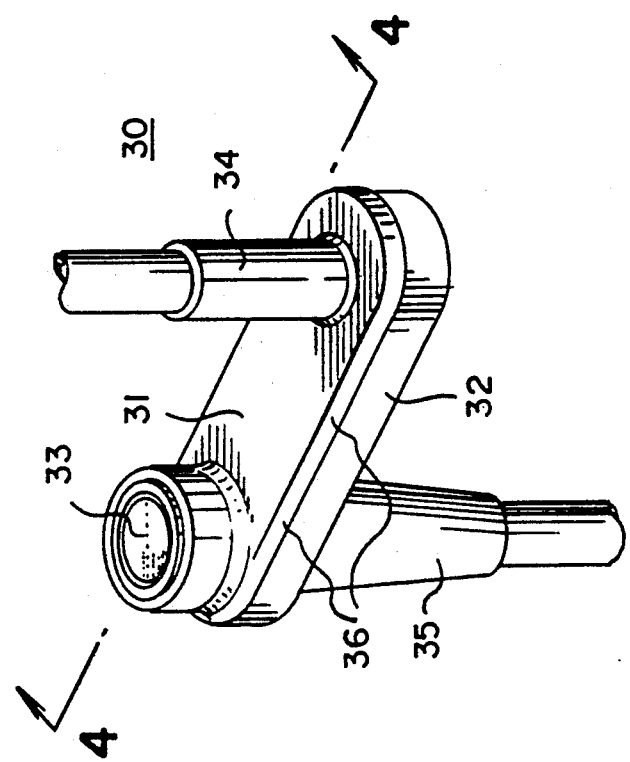
FIG. 3 is a perspective view of a flow control device in accordance with the invention.

In order to simplify directional flow control, the invention provides the two-part device 30 shown in FIG. 3. The device 30 includes a first part 31 joined to a second part 32 by ultrasonic welding. Within the device 30 are a freely floatable diaphragm (not visible in FIG. 3) and a stopper 33 for an injection site.

The diaphragm is housed on one side by an inlet sleeve 34 of the part 31 that surrounds supporting structure in the part 32. A horizontal passageway within the housing 31-32 extends from the inlet sleeve 34 to an outlet sleeve 35. Fluid flows diaphragm vertically downward in the sleeve 34, through the diaphragm into the horizontal passageway of an extension 36, then downwardly through the outlet sleeve 35 As a result, tubing attached to the inlet sleeve 34 of the housing, and to the outlet sleeve at the stopper portion of the housing are approximately parallel to one another.

Since the tubing generally hangs vertically, the stopper 33 will generally be positioned at the top of the injection site where it is easily accessible to medical personnel. As an intravenous solution leaves the valve within the housing 31-32, it makes an approximately right-angle turn and moves directly across the bottom of the stopper 33. The fluid flow forces substantially all air below the stopper 33 into the outlet sleeve 35. The injection site is thus self-priming. In a number of prior art injection sites, particularly those with a sleeve stoppers, cavities located at the centers of the stoppers prevented self-priming. With a sleeve stopper, even a liquid stream directed across the bottom of the stopper cannot expel air located within a cavity. Air has to be removed in such a case by inverting the injection site, while manually tapping the housing.

Figure 4:
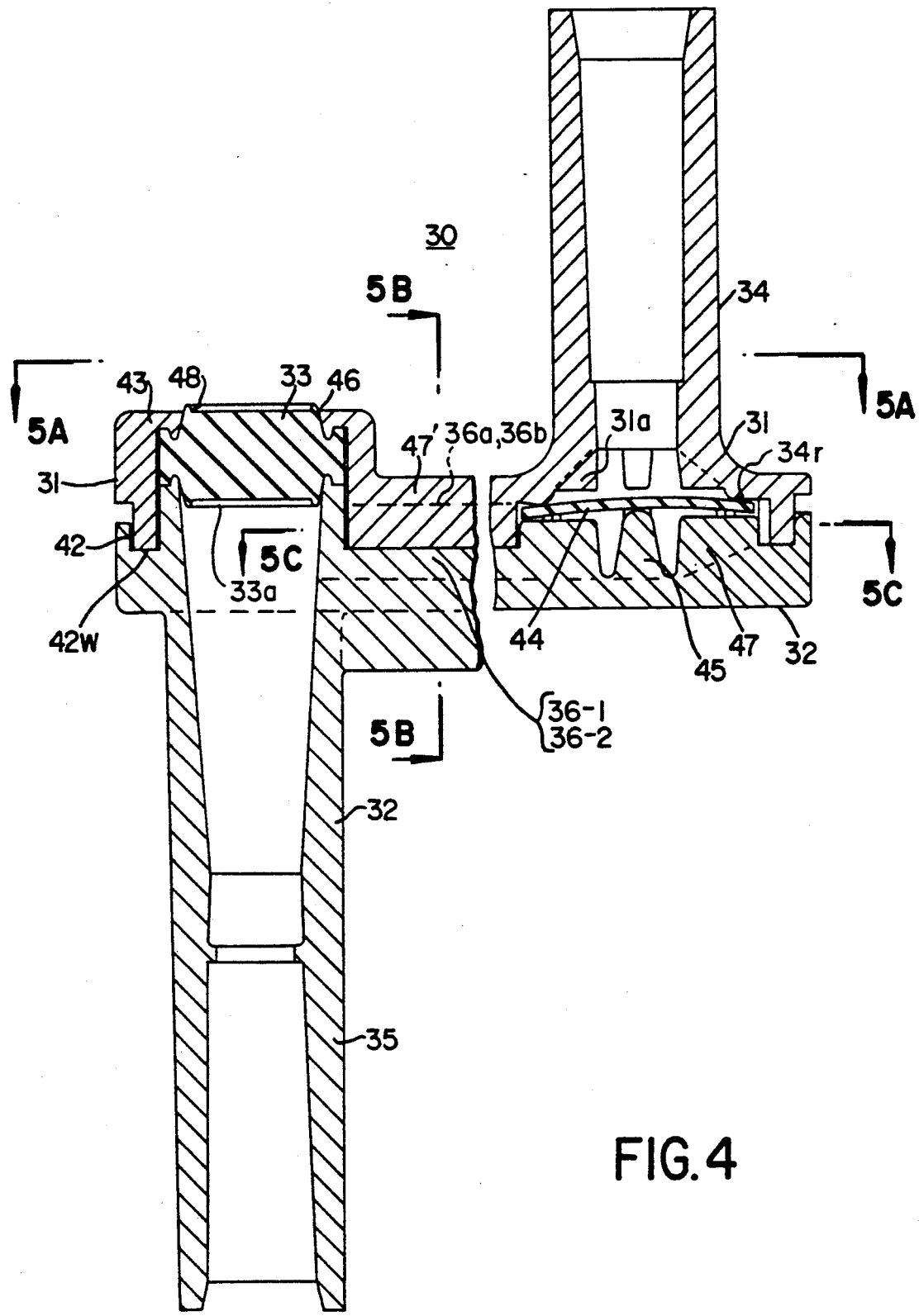
FIG. 4 is a cross-sectional view of the directional flow control and coupling device of FIGS. 3 and 5a taken along the lines 4—4.

A cross-sectional view of the device 30 of FIG. 3 is shown in FIG. 4. The raised center of the stopper 33 facilitates sterilization by providing easier accessibility for wiping with an antimicrobial agent, such as isopropyl alcohol. Prior art injection sites with stoppers recessed below the tops of injection sites allow antimicrobial agents to accumulate in puddles on the tops of stoppers. Particulate matter may also collect on recessed stoppers and be transmitted from the injection site to intravenous solution when the stopper is pierced by a needle. A raised stopper permits a clean drain of antimicrobial agents.

In addition, as shown in FIG. 4, the raised center 46 has an embossed ring 48 that provides a perffered target for insertion of a needle. Such a needle exerts a force that is generally small enough that it does not reposition or remove the stopper 33. The housing 31 that receives the stopper 33 is molded as one unit and forms a cap 43 for the stopper 33. In addition, the unitary housing 31 extends to the inlet sleeve 34 and forms a cover 47 for the passageway 36 that extends from the diaphragm 44 to the vacinity of the base of the stopper 33.

To complete the structure 30, a unitary housing 32 is ultrasonically welded to the upper housing 31. The ultrasonic welds 42w are are the base of a trough 42 which extends completely around the upper portion of the housing 32. Because the device 30 is formed by two-part housing 31-32 assembly of the device is relatively simple as compared with the complexity of the assembly required for the prior art directional flow control valves like those shown in FIG. 2. The assmebly is readily accomplished by inserting the stopper 33 into the cap 46 of the member 31 and simultaneously inserting the diaphragm 44 against a ring seat 34r of the sleeve 34. The second member 32 is then seated against the member 31 and the ultrasonic welding accomplished. By contrast with the prior are directional flow control valve of FIG. 1, the diaphragm 44 is freely floatable and is not pinned to one side of the valve structure. The free floatability of the diaphragm 44 assures positive seating fo the diaphragm, which is under a prescribed amount of bias, i.e., equilibrium pressure provided by the central pin 45 in the base of the member 32. In addition, the base includes butresses 47 which permit the diaphragm to be opened by pressure in the inlet sleeve 44 of low magnitude. This provides what is known as a "low cracking pressure" valve. Once the diaphragm 44 is opened, the inlet flow is guided by the dual passageway 36-1 and 36-2 to the base of the stopper 33 at the closed end of the outlet sleeve 35.

A cross-sectional view of FIG. 3 taken along the lines 5A—5A of FIG. 4 is shown in FIG. 5A. The dual channel passageway between the diaphragm 44 and the stopper 33 is shown in the cross-sectional view of FIG. 5B, taken along the lines 5B—5B of FIG. 4. A planned sectional view showing the dual passageway 36-1 and 36-2, along with the butresses 47 that achieve low cracking pressure shown in FIG. 5C which corresponds to the section indicated by the lines 5C—5C in FIG. 4.

Other aspects of the invention will be apparent to those of ordinary skills in the art.

What is claimed is:

1. A flow control device comprising
a first channel for the flow of fluid;
a branch channel connected to said first channel and angularly disposed with respect thereto to serve as a conduit for at least a portion of the flow from said first channel; and
means at the convergence of the branch and first channels for controlling the flow from said first channel into said branch channel, comprising a diaphragm which is nominally positioned on a ring seat and bowed under pressure into said first channel, said diaphragm making tangential contact with said ring seat that slopes away from both sides of said contact;
said branch channel having opposite ends, of which one end is connected to said first channel and the other end is connected to a second channel, with the length of said branch channel exceeding the maximum diameter of the first and second channels;
said branch channel being formed by a plurality of distinctive subordinate and enclosed channels in order to permit a substantial flow of fluid into said second channel while limiting the extent to which said diaphragm can be drawn into said branch channel under conditions of substantial fluid flow.

2. Apparatus as defined in claim 1 wherein said second channel is terminated in a cap which has a central surface communicating with said second channel and said branch channel has a flow surface that is aligned with the central surface of said cap thereby to provide for the purging of said second channel by flow into said first channel through said branch channel and across said central surface of said cap.

3. A flow control device which comprises
(a) a first channel for the control of fluid;
(b) a ring seat within said first channel;
(c) a control diaphragm in tangential contact with said ring seat;

wherein said ring seat slopes away from said control diaphragm on both sides of the tangential contact therewith and radially extending buttresses are positioned opposite said ring seat with said diaphragm therebetween, with said radially extending buttresses circumferentially disposed about said first channel and extending on both sides of the tangential contact of said diaphragm with said ring seat.

4. Apparatus as defined in claim 3 wherein said buttresses are equally distributed with respect to the circumference of said first channel and the interval between said buttresses is tapered to limit the extent to which a gasseous fluid can become entrapped between said buttresses.

5. A flow control device as defined in claim 3 wherein said diaphragm is surrounded by means that limits the lateral displacement of said diaphragm to avoid having said diaphragm become trapped in an inoperative position when said diaphragm is displaced from said ring seat by fluid flow in said first channel.

6. A flow control device as defined in claim 5 wherein said means includes openings there to enhance flow through said first channel when said diaphragm is displaced from said ring seat, with each comprising a limited width is less than the distance between openings.

7. Apparatus as defined in claim 3 wherein said radially extending buttresses are positioned opposite said ring seat with said diaphragm therebetween and extending therebeyond.

8. A flow control device which comprises
 (a) a first channel for the control of fluid;
 (b) a ring seat within said first channel;
 (c) a control diaphragm in tangential contact with said ring seat;
 wherein said ring seat slopes away from said control diaphragm on both sides of the tangential contact therewith, further including a branch channel having a plurality of conduits therein extending at an angle with said ring seat at the tangency thereof with said diaphragm, a second channel joined to said first channel by said branch channel, an injection site stopper joined to said second channel with its lower surface in alignment with said branch channel, said device being in two parts with each part containing a portion of each conduit and joined together with said conduits of the two parts in registration.

9. Apparatus as defined in claim 8 wherein said first channel has a central axis and said diaphragm is bowed under pressure by a single prong positioned along said central axis of said first channel and extends into said first channel.

10. Apparatus as defined in claim 9 wherein said diaphragm is displaced towards radially extending buttresses by said prong, thereby to limit the extent to which pressure exerted against said diaphragm in the vicinity of said prong can force said diaphragm into said first channel.

11. Apparatus as defined in claim 10 wherein said buttresses are positioned in a closed end of said first channel, extending radially from the central axis of said first channel and are circumferentially disposed with respect to said first channel.

12. Apparatus as defined in claim 11 wherein said buttresses are equally distributed with respect to the circumference of said first channel and the interval between said buttresses forming said closed end is tapered.

13. A flow control device as defined in claim 8 wherein radially extending buttresses are positioned opposite said ring seat with said diaphragm therebetween.

14. A flow control device as defined in claim 13 wherein said radially extending buttresses are circumferentially disposed about said first channel and extend on both sides of the tangential contact of said diaphragm with said ring seat.

* * * * *